United States Patent
Lietz et al.

(10) Patent No.: US 10,868,950 B2
(45) Date of Patent: Dec. 15, 2020

(54) SYSTEMS AND METHODS FOR OPERATING VIDEO MEDICAL SCOPES USING A VIRTUAL CAMERA CONTROL UNIT

(71) Applicant: KARL STORZ Imaging, Inc., Goleta, CA (US)

(72) Inventors: Daniel Lietz, Santa Barbara, CA (US); Eric Hale, Vancouver, WA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 85 days.

(21) Appl. No.: 16/217,686

(22) Filed: Dec. 12, 2018

(65) Prior Publication Data
US 2020/0195834 A1    Jun. 18, 2020

(51) Int. Cl.
| H04N 9/47 | (2006.01) |
| H04N 5/232 | (2006.01) |
| A61B 1/00 | (2006.01) |
| A61B 1/045 | (2006.01) |
| H04N 5/225 | (2006.01) |

(52) U.S. Cl.
CPC ..... *H04N 5/23206* (2013.01); *A61B 1/00009* (2013.01); *A61B 1/00011* (2013.01); *A61B 1/045* (2013.01); *H04N 5/23216* (2013.01); *H04N 2005/2255* (2013.01)

(58) Field of Classification Search
CPC ... G06T 1/20; G06T 2207/10004; G06T 7/11; G09G 3/2088; G09G 3/3644; G09G 5/00; G09G 5/36; H04N 5/225; H04N 7/18
USPC ........................................................ 348/72
See application file for complete search history.

(56) References Cited

U.S. PATENT DOCUMENTS
| 6,417,857 B2 | 7/2002 | Finger |
| 7,119,810 B2 | 10/2006 | Sumanaweera |
| 8,266,333 B1 | 9/2012 | Wade |
| 8,633,975 B2 | 1/2014 | Amling |
| 8,803,892 B2 | 8/2014 | Urbach |
| 2007/0282165 A1 | 12/2007 | Hopkins |
| 2009/0156934 A1 | 6/2009 | Lee |

(Continued)

FOREIGN PATENT DOCUMENTS
| WO | 2015163171 A1 | 10/2015 | |
| WO | 2015188275 A1 | 12/2015 | |
| WO | WO-2018203473 A1 * | 11/2018 | ......... A61B 1/00009 |

OTHER PUBLICATIONS

Sigurd, Karin; Extended European Search Report, dated Apr. 30, 2020, pp. 1-10, Munich Germany, Application No. 19215816.0-1122.

*Primary Examiner* — Gims S Philippe
(74) *Attorney, Agent, or Firm* — Michael J. Loi (57) ABSTRACT

A method of operating video scopes using graphics processing unit (GPU) resources of a virtual camera control unit (CCU) server connected to a network includes determining an available amount of GPU resources; providing a primary scope to connect to the network, the primary scope including a primary scope setting adjustable within a range from a minimum level that requires a minimum amount of GPU resources to a maximum level that requires a maximum amount of GPU resources; configuring the primary scope setting to a primary scope first level; determining a first desired amount of GPU resources based on the primary scope first level; and comparing the first desired amount of GPU resources with the available amount of GPU resources.

24 Claims, 9 Drawing Sheets

(56) References Cited

U.S. PATENT DOCUMENTS

| | | |
|---|---|---|
| 2009/0179985 A1 | 7/2009 | Amling |
| 2014/0325073 A1 | 10/2014 | Urbach |
| 2016/0086357 A1* | 3/2016 | Park .................... G06T 11/006 382/131 |
| 2017/0046847 A1* | 2/2017 | Yamane .................. G09G 5/36 |
| 2018/0253870 A1* | 9/2018 | Park .................... G06T 11/003 |
| 2020/0060523 A1* | 2/2020 | Matsuda ................ A61B 34/20 |

* cited by examiner

SYSTEMS AND METHODS FOR OPERATING VIDEO MEDICAL SCOPES USING A VIRTUAL CAMERA CONTROL UNIT

TECHNICAL FIELD OF THE INVENTION

The invention relates generally to the field of medical devices and more specifically to the field of video medical scopes and their controllers.

BACKGROUND OF THE INVENTION

Video medical scopes, such as endoscopes, are typically set p in an operating room or exam room with an associated controller, referred to herein as a camera control unit (CCU). The video medical scope usually has a cable that plugs into the controller for sending video data and button interface data from the scope to the controllers, and receiving commands from the controller. The controller processes video data from the scope to filter, enhance, and analyze the video imagery in a variety of ways. The CCU is usually carried on a rack that is wheeled into the operating room and set up by a medical technician who connects the video medical scope to the CCU and configures it for a particular procedure. Such a process adds delay and complexity to surgical preparations, and further increases the amount of medical equipment that must be cleaned and sterilized to operate safely.

The upgrade and development process of CCU systems also has complexities. Existing CCU systems are created based on a complex development flow of FPGA, CPU and image processing development leading to long and risky development times. Graphics processing unit (GPU) based CCU units may also provide equivalent capabilities. Scaling these systems into higher performance systems becomes difficult when new video technology is introduced, such as high definition video like the 2K or 4K video standards. These systems also spend a large portion of time effectively idle.

SUMMARY OF THE INVENTION

It is an object of the invention to provide improvements to manage and control video medical scopes within a hospital or clinic type environment. Another object of the invention to improve the setup speed and cost for video medical scopes. It is another object of the invention to provide more efficient use of processing power for video medical scope imaging. Further, it is an object of the invention to allow development of improvements for video medical scope image processing to be deployed quickly and easily.

A method of operating video scopes using graphics processing unit (GPU) resources of a virtual camera control unit (CCU) server connected to a network includes determining an available amount of GPU resources; providing a primary scope to connect to the network, the primary scope including a primary scope setting adjustable within a range from a minimum level that requires a minimum amount of GPU resources to a maximum level that requires a maximum amount of GPU resources; configuring the primary scope setting to a primary scope first level; determining a first desired amount of GPU resources based on the primary scope first level; and comparing the first desired amount of GPU resources with the available amount of GPU resources.

In other features, the method of claim includes allocating the first desired amount of GPU resources from the available amount of GPU resources when the first desired amount of GPU resources is less than or equal to the available amount of GPU resources and operating the primary scope using the primary scope first level.

In still other features, the method includes adjusting the primary scope setting from the primary scope first level to a primary scope second level that is less than the primary scope first level when the first desired amount of GPU resources is greater than the available amount of GPU resources.

In yet other features, the primary scope includes a plurality of primary scope settings, each primary scope setting adjustable within a range from a minimum level to a maximum level, further comprising prioritizing the plurality of primary scope settings in order of importance based on user input. The method further includes selecting a first primary scope setting of the plurality of primary scope settings based on the prioritizing and adjusting the first primary scope setting from the primary scope first level to a primary scope second level that is less than the primary scope first level.

In other features, the method includes prompting to increase the available amount of GPU resources when the first desired amount of GPU resources is greater than the available amount of GPU resources.

In yet other features, the method includes determining a locked amount of GPU resources, the available amount of GPU resources not including the locked amount of GPU resources. The method includes comprising prompting a user to unlock a first portion of the locked amount of GPU resources when the first desired amount of GPU resources is greater than the available amount of GPU resources. The method includes determining the first portion based on a difference between the available amount of GPU resources and the first desired amount of GPU resources.

In still other features, the method includes providing a secondary scope to connect to the network, the secondary scope including a secondary scope setting adjustable within a range from a minimum level that requires a minimum amount of GPU resources and a maximum level that requires a maximum amount of GPU resources; configuring the secondary scope setting to a secondary scope first level; determining a second desired amount of GPU resources based on the secondary scope first level; determining a total desired amount of GPU resources based on the first desired amount of GPU resources and the second desired amount of GPU resources; and comparing the total desired amount of GPU resources with the available amount of GPU resources.

In other features, the method further includes allocating the first desired amount of GPU resources from the available amount of GPU resources when the first desired amount of GPU resources is less than or equal to the available amount of GPU resources and operating the primary scope using the primary scope first level.

In yet other features, the method further includes comprising allocating the second desired amount of GPU resources from the available amount of GPU resources when the total desired amount of GPU resources is less than or equal to the available amount of GPU resources and operating the secondary scope using the secondary scope first level.

In other features, the method further includes comprising adjusting the secondary scope setting from the secondary scope first level to a secondary scope second level that is less than the secondary scope first level when the total desired amount of GPU resources is greater than the available amount of GPU resources.

In other features, the secondary scope includes a plurality of secondary scope settings, each secondary scope setting adjustable within a range from a minimum level to a maximum level, further comprising prioritizing the plurality of secondary scope settings in order of importance based on user input. The method includes selecting a first secondary scope setting of the plurality of secondary scope settings based on the prioritizing and adjusting the first secondary scope setting from the secondary scope first level to a secondary scope second level that is less than the secondary scope first level.

In yet other features, the method includes prompting to increase the available amount of GPU resources when the total desired amount of GPU resources is greater than the available amount of GPU resources.

In still other features, the method includes determining a locked amount of GPU resources, the available amount of GPU resources not including the locked amount of GPU resources. The method includes prompting a user to unlock a first portion of the locked amount of GPU resources when the total desired amount of GPU resources is great than the available amount of GPU resources. The method includes determining the first portion based on a difference between the available amount of GPU resources and the total desired amount of GPU resources.

A system for operating video scopes using graphics processing unit (GPU) resources of a virtual camera control unit (CCU) server connected to a network includes an allocation manager, a primary scope, a feature module, and a load balance module. The allocation manager determines an available amount of GPU resources. The primary scope includes a primary scope setting adjustable within a range from a minimum level that requires a minimum amount of GPU resources to a maximum level that requires a maximum amount of GPU resources. The feature module configures the primary scope setting to a primary scope first level. The load balance module determines a first desired amount of GPU resources based on the primary scope first level and compares the first desired amount of GPU resources with the available amount of GPU resources.

In other features, the allocation manager allocates the first desired amount of GPU resources from the available amount of GPU resources when the first desired amount of GPU resources is less than or equal to the available amount of GPU resources.

In yet other features, the feature module adjusts a primary scope first setting from the primary scope first level to a primary scope second level that is less than the primary scope first level when the first desired amount of GPU resources is greater than the available amount of GPU resources.

In still other features, the primary scope includes a plurality of primary scope settings, each primary scope setting adjustable within a range from a minimum level to a maximum level, further comprising a prioritization module that prioritizes the plurality of primary scope settings in order of importance based on user input. The feature module selects a first primary scope setting of the plurality of primary scope settings based on the prioritizing and adjusts the first primary scope setting from the primary scope first level to a primary scope second level that is less than the primary scope first level. The load balance module prompts to increase the available amount of GPU resources when the first desired amount of GPU resources is greater than the available amount of GPU resources.

In order to achieve these objects, the present invention provides systems, devices, methods, and program products for operating video medical scope devices without a local camera control unit (CCU), and instead providing virtual CCU's through a virtual CCU server across a network, connecting to the scope and to a display/user interface located in the room with the scope. The server is provided with multiple GPU's that are allocated to instantiations of a virtual CCU. The number of GPU's may be adapted based on the expected processing needs of the virtual CCU or based on actual processing workload. An adapter may be provided for legacy scopes to connect, having the legacy scope control and video transmission protocol at the scope side, and an optical network interface for transmitting video and control data back and forth to the server. By centralizing the processing and allocating processing power only as needed for specific tasks, it reduces the physical setup time to move a traditional tower in and out of an operating room along with any sterilization required. Further, development and deployment of improved CCU software is improved both in cost and speed to develop and deploy.

Implementations of the invention may also be embodied as software or firmware, stored in a suitable medium, and executable to perform various versions of the methods herein. These and other features of the invention will be apparent from the following description of the preferred embodiments, considered along with the accompanying drawings.

DETAILED DESCRIPTION OF EXAMPLE EMBODIMENTS

Systems, devices, methods, and program products are provided for operating video medical scope devices without a local camera control unit (CCU), and instead providing virtual CCU's through a virtual CCU server across an optical network, connecting to the scope and to a display/user interface located in the room with the scope. The server is provided with GPU resources comprising multiple GPU's that are allocated to instantiations of a virtual CCU. This avoids moving CCU equipment into an operating room or examination room each time the equipment is needed. It also provides a more efficient use of resources because a virtual CCU server can be configured with only the processing power sufficient to operate those virtual CCU's that may be required at the same time, versus providing mobile CCU racks in a much greater number to have sufficient racks of the various models and capabilities that may be required available in any area of hospital or clinic. The number of GPU's allocated to a virtual CCU may be adapted based on the expected processing needs of the virtual CCU or based on actual processing workload. An adapter may be provided for legacy scopes to connect, having the legacy scope control and video transmission protocol at the scope side, and an optical network interface for transmitting video and control data back and forth to the server.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module refers to an application specific integrated circuit (ASIC), a field programmable gate array (FPGA), an electronic circuit, a processor (shared, dedicated, or group) and memory that execute one or more software or firmware programs, a combinational logic circuit, or other suitable components that provide the described functionality.

Figure 1:
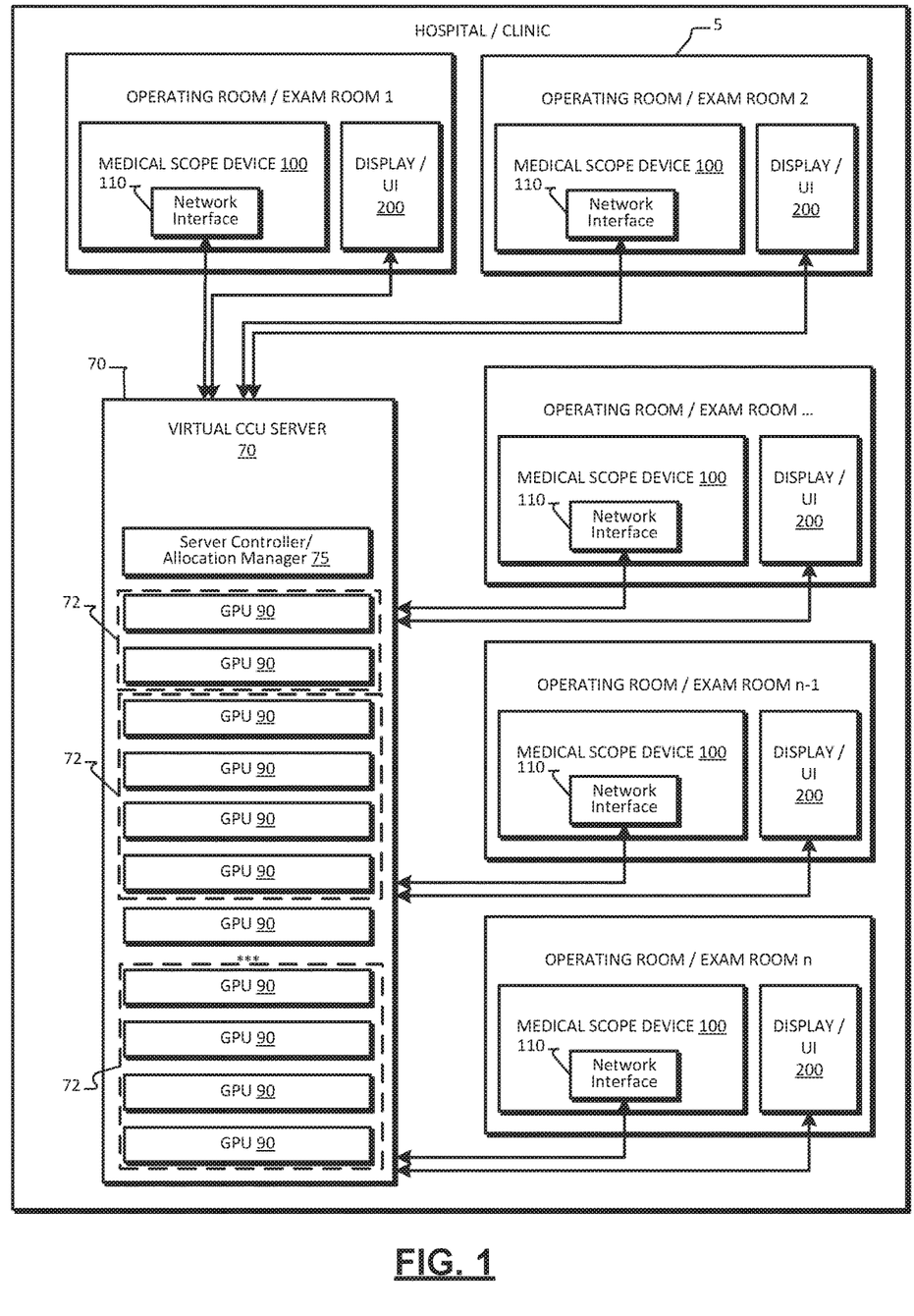
FIG. 1 is a block diagram of a system of connected medical devices in a hospital according to an example embodiment of the invention.

FIG. 1 is a system block diagram of a medical camera system in the context of a hospital or clinic in which the system is employed according to an example embodiment. In this version, the medical camera system includes multiple video medical imaging devices such as a video medical scope 100 (hereafter scope 100), each having an associated display/UI 200, which may include one or more video displays and user interface devices such as mice, keyboards, button pads, and joysticks. As depicted, the scope 100 and display/UI 200 may be operational in an exam or operating room 5. Multiple scopes 100 and display/UI 200 may be in multiple exam or operating rooms 5 connect by a network to a virtual camera control unit (CCU) server 70 comprising a plurality of GPUs 90 for providing the operator interface and control, as well as image processing functions from a central location rather than a CCU device, typically mounted in a rack, being present in the operating room. The virtual CCU server 70 is typically located in a hospital server room. While virtual CCU server 70 may be located outside of the hospital or clinic in which the procedures are performed, typically it will be located in the building or at least on the same site or facility, such as, for example, in data center on the grounds of a larger medical complex. While the drawing shows one scope 100 in each room 5, this is not limiting and multiple video medical scopes 100 may be used in a single room 5 simultaneously if network connectivity allows. Thus, each scope 100 may be connected to GPU resources of the virtual CCU server 70 as needed.

Each scope 100 is communicatively coupled to a modulator in their respective network interfaces 110, which may be integrated with the scope or in an external adapter, the modulator modulating at least control data and video data from each respective scope 100 for transmitting on the network to the virtual CCU server 70. Demodulators in the network interfaces 110 receive network traffic, typically only from the virtual CCU server. There are one or more display/UI 200 associated with a respective scope 100. Instead of the prior art arrangement of connecting the scope 100 by cable to a local CCU which is connected to the displays, the present system provides the virtual CCU server 70 communicatively coupled to the video medical scopes 100 and display/UI 200 across the network, through the optical modulators in their respective network interfaces. Thus, the The invention may be embodied as a system such as the example system depicted, or as a server for providing virtual CCUs over a network to multiple video medical scope devices. The invention may also be embodied as tangible, non-transitory program code operable for controlling the virtual CCU server to perform its functionality in cooperation with the other devices. The virtual CCU server 70 is programmed and constructed to provide a virtual CCU 72 for each scope 100, the virtual CCU 72 including one or more GPUs 90 executing program code similar to that which would be provided in a local CCU. That is, the virtual CCU 72 is operable to receive the raw image data from the scope 100, for example in the form of serialized frame data, manipulate visual characteristics of the video data via image or video processing, encode the manipulated video data, and process the control data, to output the encoded manipulated video data to the respective associated video displays over the optical network, and to output the processed control data to the respective video medical scope for controlling an operational aspect of the respective video medical scope.

The one or more GPUs 90 are preferably allocated or assigned to a respective virtual CCU 72 dynamically by the server controller and allocation manager 75. Such allocation is typically done upon connection and configuration of the scope 100 for the procedure required, as further described below.

Figure 2:
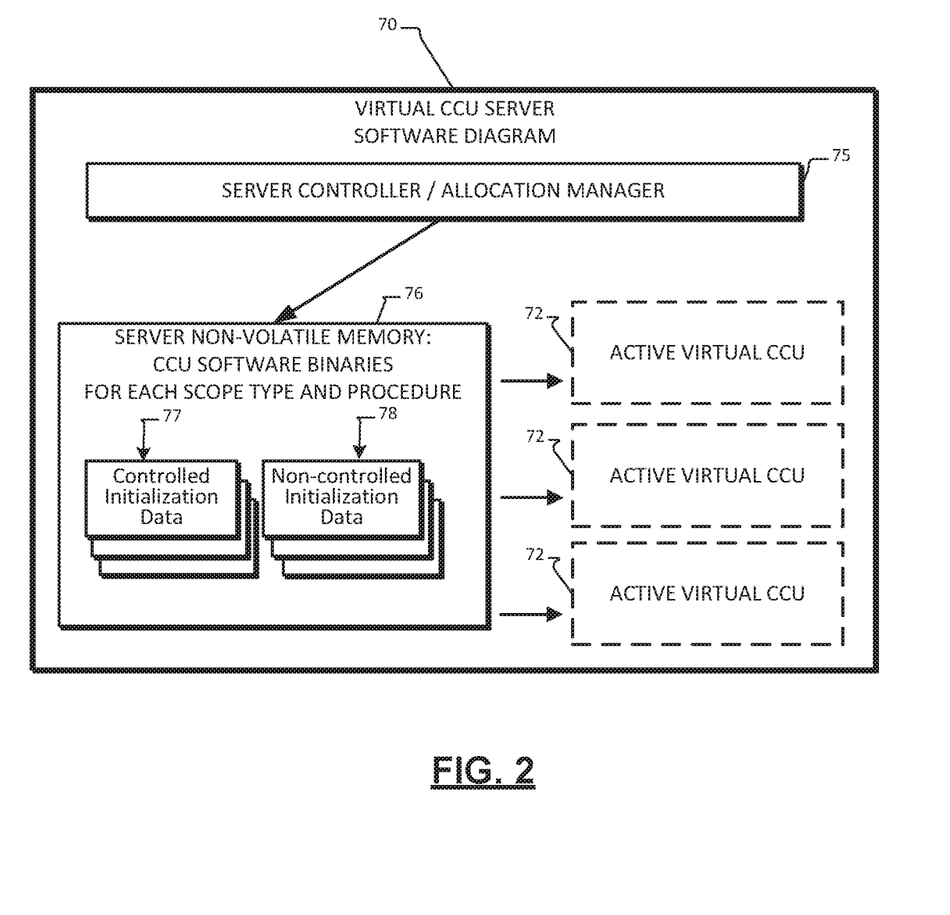
FIG. 2 is a block diagram of a virtual CCU server software architecture.
Figure 3:
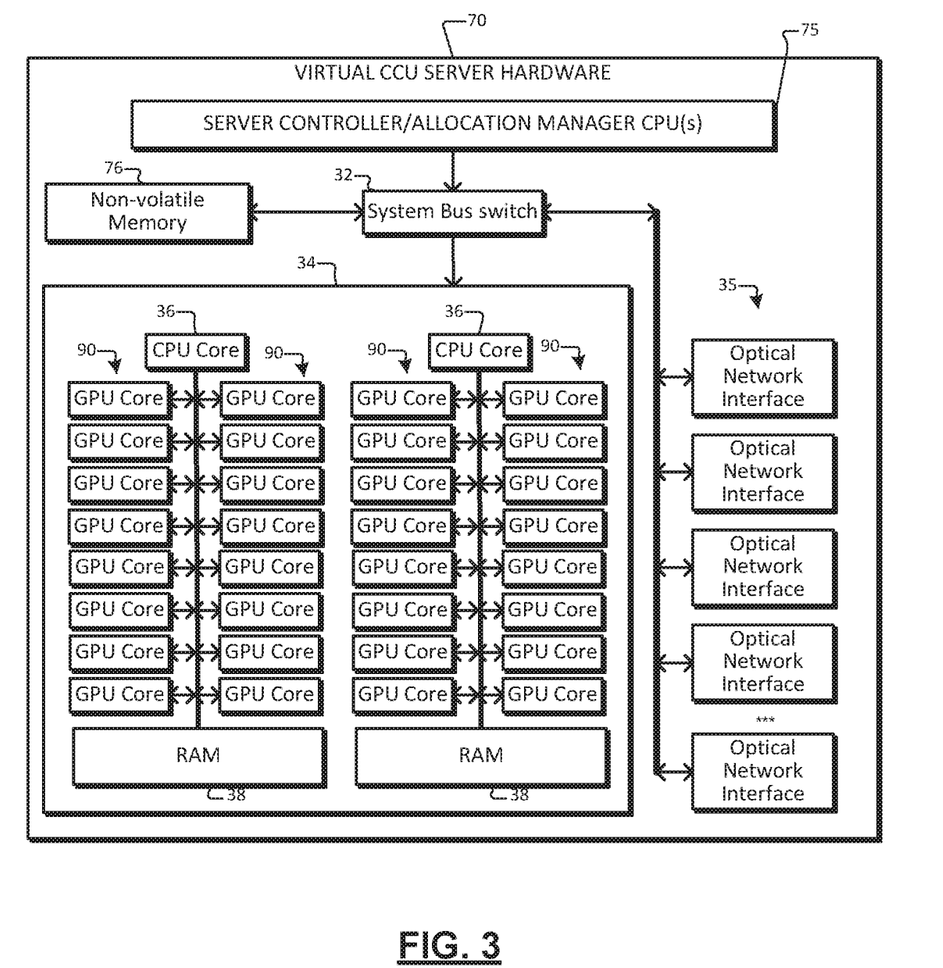
FIG. 3 is a block diagram of the same server's hardware architecture.
Figure 4:
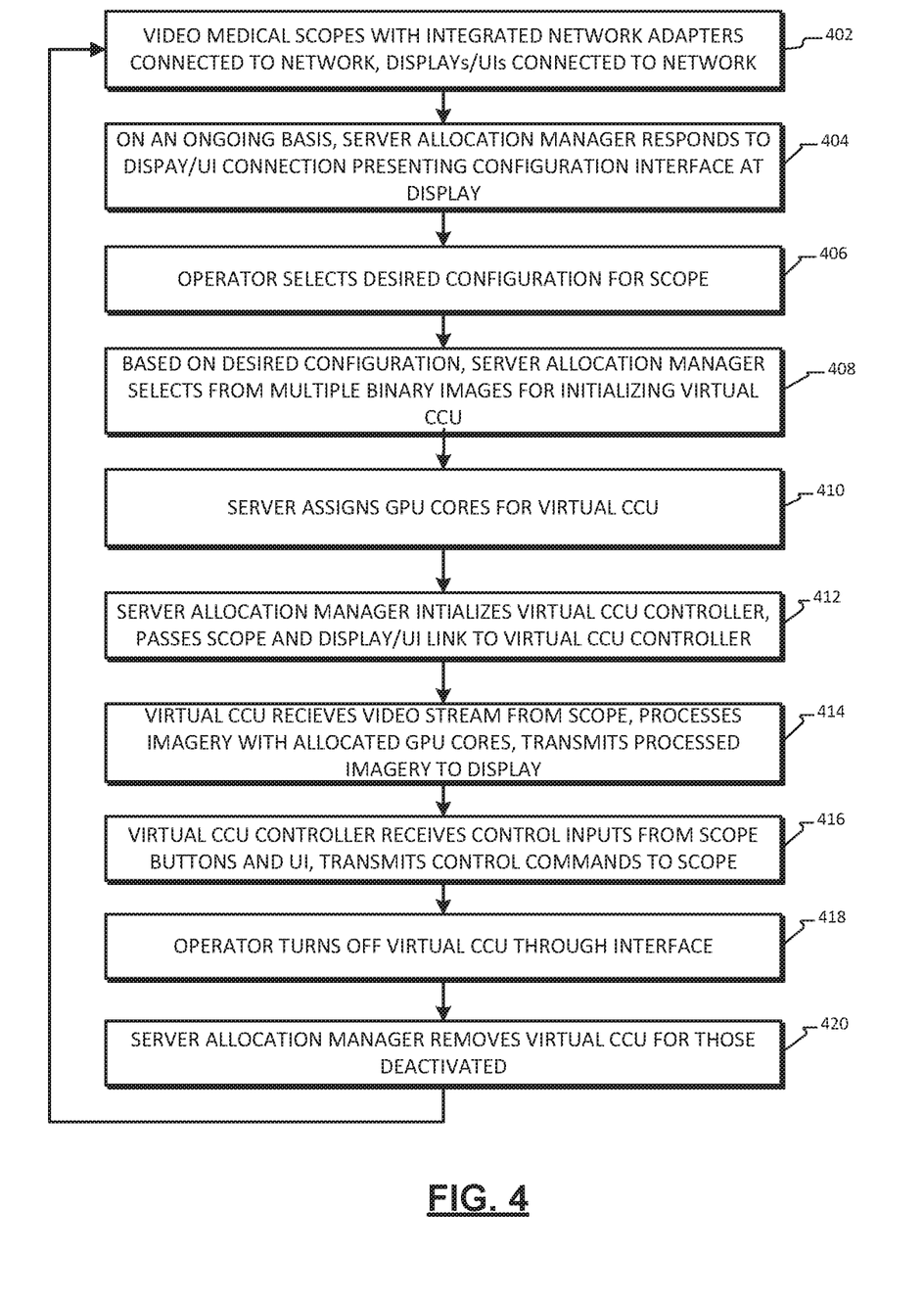
FIG. 4 is a software flowchart of a process for initiating and operating a virtual CCU.

The virtual CCU server 70 will now be described further with respect to FIGS. 2-4. FIG. 2 is a block diagram of the virtual CCU server software architecture. FIG. 3 is a block diagram of the same server's hardware architecture. FIG. 4 is a software flowchart of a process for initiating and operating a virtual CCU. The general design of GPU server hardware and software is known in the art, and therefore the common elements such as the operating system, internal chipsets and power supplies will not be described here in order to avoid obscuring the relevant portions of the hardware and software.

Referring to FIG. 2, a virtual CCU server 70 includes an allocation manager 75 including server manager software, which may be executed by a separate dedicated server CPU processor within virtual CCU server 70, or may be executed by a CPU portion of a CPU/GPU server device. Virtual CCU server 70 also includes non-volatile memory 76, such as a hard drive or flash drive, holding initialization code and initialization settings for virtual CCUs. The virtual CCU code typically is stored in the form of boot images or binary images containing executables but may be a mix of files and database information such as configuration settings necessary to initialize GPU cores on the virtual CCU server to perform as a virtual CCU 72. The phrase "binary image" describes binary data such as a file or group of files used to configure (e.g., boot or initialize) the virtual CCU 72, and is not used in the sense of a picture image. Such initialization code or information will be referred to as initialization data.

In the depicted version, the non-volatile memory 76 holds a set of controlled initialization data 77 and a set of non-controlled initialization data 78. Each binary image or other initialization data in the set may be used to instantiate a virtual CCU 72 suitable for use with a particular video medical scope model to perform a particular procedure. The term 'controlled' refers to the regulatory control that is applied to some video medical scope software. Various medical procedures require electronic systems and associated software and firmware to be regulated by the FDA or other regulatory bodies and thus strictly controlled. For example, endoscopic fluorescence imaging systems capable of auto-fluorescence, fluorescent imaging (FI), and/or Photodynamic Diagnosis (PDD) procedures are currently classified as an FDA Class III medical device, which is governed by a Premarket Approval (PMA) release and approval process. Because of the risk profile of Class III devices, Class III devices are "locked down" such that no changes to system hardware, programmable hardware such as field-programmable-gate-array (FPGA) devices, or software are allowed without further FDA approval.

In some cases, the algorithm to perform a particular image processing technique is strictly controlled while the hardware platform itself is not subject to the same regulations and testing. Because any update to a controlled binary requires regulatory approval which can take six to twelve months to obtain, those procedures that do not require controlled software are typically stored separately and may have software and firmware updates without regulatory approval. Controlled initialization data 77 holds binary images or other files and data to instantiate virtual CCU configurations that are subject to PMA controls. Non-controlled initialization data 78 holds binary images or other files and data to instantiate various virtual CCU configurations that are not PMA controlled, that is that do not require class III pre-market approval. While these types of initialization data are shown, some systems may only store one type of data, and the storage process may not differentiate between the regulatory types of the binary images stored. Typically, the difference is relevant during the initialization stage of a virtual CCU, where the initialization procedure must perform a verification to check that the controlled image matches the one that has been approved for such operations.

Multiple virtual CCU's 72 may be instantiated and active at any particular time on a virtual CCU server 70, up to the limit of the processing capacity provided on the server. A virtual CCU 72 includes a running copy or instantiation of software and/or firmware, running on allocated hardware to perform CCU functionality. The initialization process is further described with respect to FIG. 4. Non-volatile memory 76 will of course hold other data such as the server operating system and software for the allocation manager 75.

Referring now to FIG. 3, a hardware block diagram for an example virtual CCU server is shown. While this particular design is shown for a virtual CCU server 70, many modern CPU/GPU server designs are suitable hardware platforms for a virtual CCU server according to the techniques herein. Virtual CCU servers 70 may be single blade servers or larger integrated platforms including integrated high-speed busses and system RAM, for example. The allocation manager 75 may run on a separate CPU card installed in a larger server with other CPU/GPU cards, or may run on one or more of the CPU's in a CPU/GPU card or other similar module. Multiple network interfaces 35 connect virtual CCU server 70 to the hospital or clinic network to which the video medical scopes 100 and displays/UI 200 are connected to complete the system. In this version, a system bus 32, such as a PCIe (Peripheral Component Interconnect Express) bus, connects the network interfaces to the various CPU and GPU cards in the server. Non-volatile memory 76 is also connected by a high-speed bus, which may be the same bus or another suitable bus. Allocation manager 75 is programmed to allocate GPUs 90 and CPU functionality, whether in dedicated CPU cores 36 or as virtual machines running on CPU cores 36. The number of GPU cores assigned to function as a particular virtual CCU 72 can vary, as shown in FIG. 1, and may be predetermined based on the image processing functions required for a particular scope configuration, or allocated dynamically based on the real-time processing load of a particular virtual CCU 72.

System bus 32 connects the optical interfaces to one or more processing devices, typically mounted on processor cards or modules in the server housing. While one processing module 34 is shown, this is not limiting and a typical CPU/GPU server may contain many such cards, such as 16 or 20 cards. The network interfaces 35 may be integrated with individual processing modules 34. The particular network protocol is not limiting, and may be, for example, a Firewire® connection carrying PCIe, for example, or an optical or high speed ethernet network carrying remote direct memory access (RDMA) signaling to enhance speed and latency in linking the data to the desired GPUs.

Typically, an individual CPU core 36 will be responsible for controlling the user interface logic and graphics processing for a respective virtual CCU 72. Such a CPU core may also multi-task or multi-thread, or include virtual machines (VM) technology, to act as the controller of more than one virtual CCU. CPU cores 36 direct the tasking of GPUs 90 to perform the CCU image processing tasks for each connected scope 100.

Typically the GPUs 90 are on the same semiconductor device as the CPU core 36 to which they are associated (combined) to instantiate their respective virtual CCU, however this is not limiting the GPUs 90 may be on separate semiconductor devices from the associated CPU core 36. GPUs 90 preferably have GPU-to-GPU interconnects such as the Nvidia NVLink® interconnecting adjacent groups of GPU cores allowing sequential execution of image processing techniques without having to relay inter-thread or inter-process messaging through system memory or the local bus. Such on-chip interconnect busses may connect each GPU core to four adjacent GPU cores, but merely connecting to at least two adjacent GPU cores is beneficial and may be done in some embodiments of the invention to allow sequential execution of graphics processing functions without requiring the graphics data to be passed on the local bus between GPUs. RAM 38 is connected by a high-speed local bus or memory bus.

Many other interconnect arrangements are possible for the GPU-RAM interconnect. For example, each GPU may have on-chip RAM or dedicated local RAM. The CPU cores 36 and GPUs 90 preferably have unified memory, allowing both to access RAM 38 for at least a portion of the RAM present on the processing module 34. The allocation manager 75 may include dedicated RAM connected by a memory bus. In some embodiments, virtual CCU server 70 may include an optical bus communicatively coupled to the optical modulator/demodulators in the network interfaces 35 and to the multiple GPUs. Such an arrangement allows higher bandwidth within the system bus and lower overall latency.

As can be understood, in operation of the system, multiple virtual CCUs may each be assigned two or more GPUs 90 having access to shared graphics processing or RAM 38, with a CPU core 36 assigned as a virtual CCU controller for coordinating tasks among the two or more GPUs 90. The respective two or more GPU's 90 assigned to the at least one virtual CCU may be individual GPU processor cores of larger processor devices, or single GPU devices mounted together on the processing module 34. While it is possible for GPU cores on different processing modules to cooperate in some CPU/GPU server architectures that have high-speed system busses allowing grouping of processors on different cards or modules, in most versions of the invention all the GPUs 90 assigned to a particular virtual CCU will be on the same processing module 34.

FIG. 4 is a software flowchart of a process for initiating and operating virtual CCUs, which may be executed on hardware such as that depicted in FIG. 3, or other suitable CPU/GPU hardware. Generally, the process provides virtual CCUs over a network to multiple video medical scope devices each having an associated one or more video displays. The process begins at block 402, where a scope 100 is connected to the network on which the virtual CCU server sits, the scope located in an operating or examination room while the server resides in a server room or data center somewhere on the network. At block 404, the virtual CCU server responds to such connections on an ongoing basis, including the process detecting the connection of each of the multiple video medical scopes on the network and responding as shown in the flowchart. The video medical scopes are typically located at different rooms than the virtual CCU server, while multiple scopes may be connected in the same operating or exam room.

For each connected video medical scope, at block 406, the process receives a selection from the operator identifying a desired CCU configuration for the scope. In some versions, a particular scope may have only a single possible configuration or the server may be pre-programmed to limit the configurations available for particular scopes, thereby skipping displaying the configuration interface at block 404 and skipping block 406 to begin a predetermined configuration at block 408. Either automatically or based on a desired CCU configuration, at block 408 the process includes selecting a respective set of configuration data for initializing a respective virtual CCUs for each of the video medical scopes. The data is typically a binary image containing executable code for a CPU core 36 and multiple GPUs 90 to instantiate and operate a virtual CCU (72). However, this is not limiting and the data may instead include only configuration parameters that configure code already present in CPU core 36 and GPU 90 memory.

Next, based on the configuration data, at block 410 the process assigns a respective set of two or more GPU cores for use in each respective virtual CCU. The number and selection of GPU cores may be contained in the configuration data such as the binary image, or may be determined by the virtual CCU server based on the expected processing load of the various image processing techniques to be performed by the virtual CCU. At block 412, the process initializes the virtual CCUs based on their respective set of configuration data and links them to their respective video medical scopes and display/UI, passing control data and a stream of video data from the respective video medical scopes to their respective virtual CCUs. This typically involves designating a CPU core (i.e. 36, FIG. 3) to act as a virtual CCU controller to direct the GPU cores and data flow, and present the interface at the display/UI 200 showing the processed video. At block 414, the respective virtual CCU operates to receive control data and the video data streaming from the video medical scope, process the video imagery with the allocated GPU cores, and transmit the processed imagery back over the network to the display.

Generally, the server operates the virtual CCUs to manipulate visual characteristics of the video data via image or video processing, encoding the manipulated video data, and processing the control data from the video medical scope buttons and from the UI associated with the display (both in the operating room or exam room) to respond to commands such as changing the video display mode or changing the operating mode of the video medical scope as shown at block 416. To change modes of the scope, the virtual CCU outputs processed control data to the respective video medical scope for controlling an operational aspect of the respective video medical scope.

The virtual CCU continues operating and responding to commands until an operator turns off the virtual CCU through the UI interface or disconnects the respective video medical scope at block 418. The server allocation manager may remove the virtual CCU and de-allocate the CPU and GPU cores when it is deactivated, or, in certain scenarios, may maintain the configuration of a particular virtual CCU while merely unlinking it from receiving data, and instantiate another, different CCU for the same operating room to support another different video medical scope.

While the process is depicted as a loop to describe the functionality, it is typically an event driven or interrupt driven process in which new events such as connection of new video medical scopes and display/UIs at other network connections with cause a different process thread to instantiate a new virtual CCU in parallel.

Figure 5:
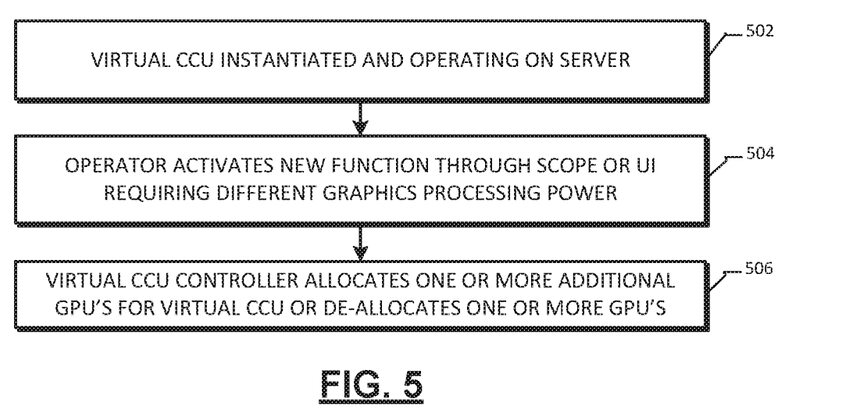
FIG. 5 is a flowchart of a process for allocating GPUs to a virtual CCU according to another embodiment.

In some embodiments, assigning the sets of GPU cores is done based on a maximum expected processing load of the respective desired CCU configuration. In some other embodiments, as shown in the flowchart of FIG. 5, the process may include, while operating a virtual CCU at the virtual CCU server at block 502, receiving respective control inputs from video medical scopes or there associated UI operable to change an operating mode of the virtual CCU at block 504, and in response assigning additional GPU cores for use in the first virtual CCU at block 506. The process may also de-allocate GPU cores if a mode change requires fewer GPU's.

Figure 6:
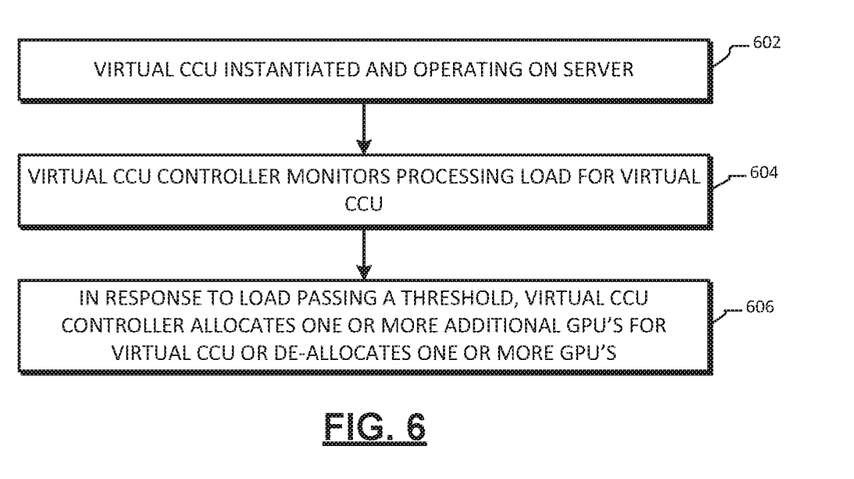
FIG. 6 is flowchart of another alternative process for allocating GPUs to a virtual CCU.

In some other embodiments, the number of GPUs allocated to a particular virtual CCU may be adjusted based on the processing load, as depicted in the flowchart of FIG. 6. In this process, when a virtual CCU is instantiated and operating on the virtual CCU at block 602, the process includes monitoring processing load levels of the respective virtual CCUs in operation at block 604 and based on the respective processing load level assigning addition GPU cores for use in respective virtual CCUs or de-allocating GPU cores. This may be done by providing thresholds of a designated processing load metric, which, when passed, will cause the number of allocated GPUs to go up or down. The metric may be the time to process a video image frame relative to the number of graphics algorithms performed on the frame, measuring an idle time of one or more of the GPUs, or the number of mathematical operations, such as floating point operations, performed. Other suitable metrics may be used.

Figure 7:
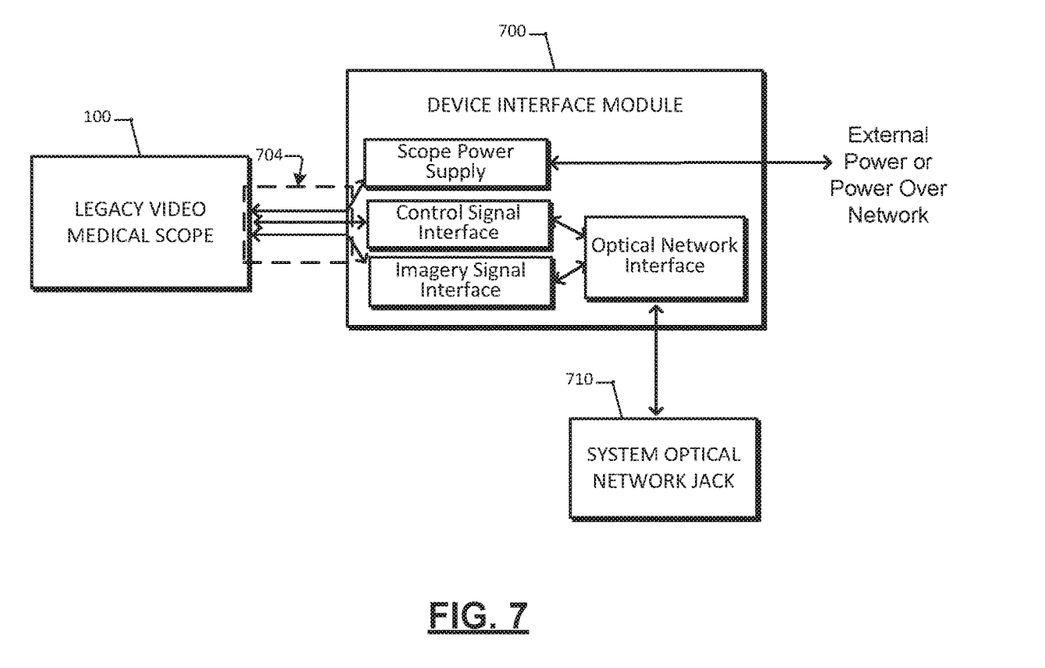
FIG. 7 is a hardware block diagram of a device interface module for connecting a legacy video medical scope to the network and virtual CCU server.

FIG. 7 is a hardware block diagram of a device interface module for connecting a legacy scope 100 to the network and virtual CCU server. The depicted device interface module 700 allows the legacy video medical scope, which does not have an optical network interface built in and uses legacy formats for video data and control signal data, to operate with the virtual CCU system described herein. Between the scope 100 and the device interface module 700 is shown an optional cable 704, shown as optional because the device interface module 700 may connect directly to the scope in a rigid manner allowing handling as a single unit, or may connect with the cable 704 allowing scope 100 to be used in its usual fashion. Device interface module 700 includes an imagery signal interface for receiving the image data from the legacy scope 100 and converting the data to a format used by the virtual CCU server. A control signal interface does the same for the control signaling, such as signals to put the scope into a particular mode like fluorescence imaging mode. This may involve converting analog signals to digital form, or translating digital signals to an alternative format. It also may involve multiplexing the signals for transmission together through the optical network interface.

Typically, the power supply for a legacy scope is also supplied through the cable connection, so a scope power supply is provided in the device interface module as well, supplied as depicted either by an external power supply or by power over the network jack in scenarios where the optical network formal also supports conductive power lines. In scenarios where a cable is used, the network interface may be integrated with a similar interface for the display/UI 200, allowing a device interface module 700 to connect scope 100 and display/UI 200 to the network. In such case, device interface 700 would typically perform multiplexing or open multiple ports to provide a data link for both the display/UI 200 and the scope 100. As can be understood, video medical scopes using a device interface module 700 can be used concurrently with the same virtual CCU server as those having an integrated network interface.

Figure 8:
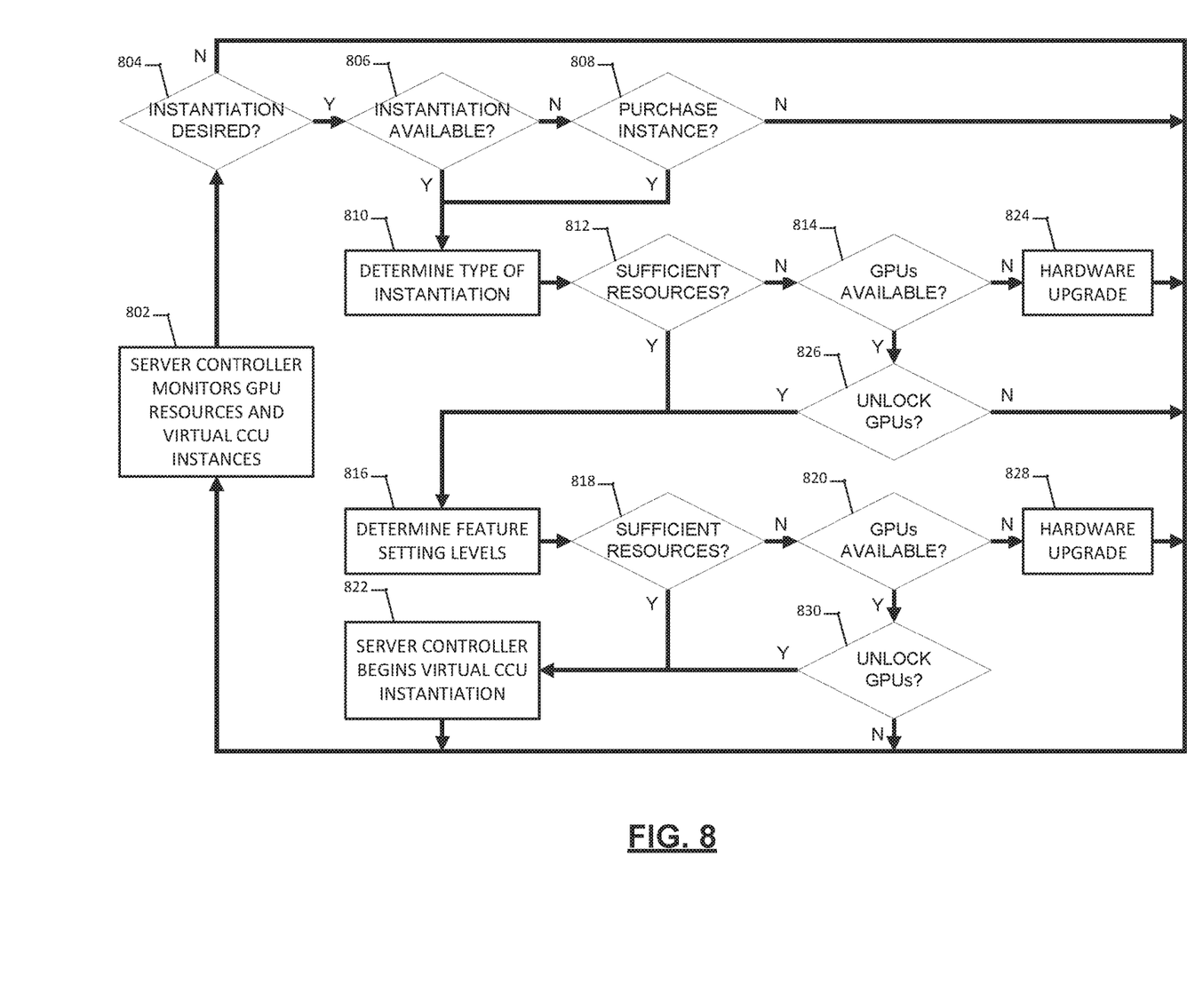
FIG. 8 is a flowchart of an exemplary embodiment of a system for controlling and allocating GPUs to a virtual CCU.
Figure 9:
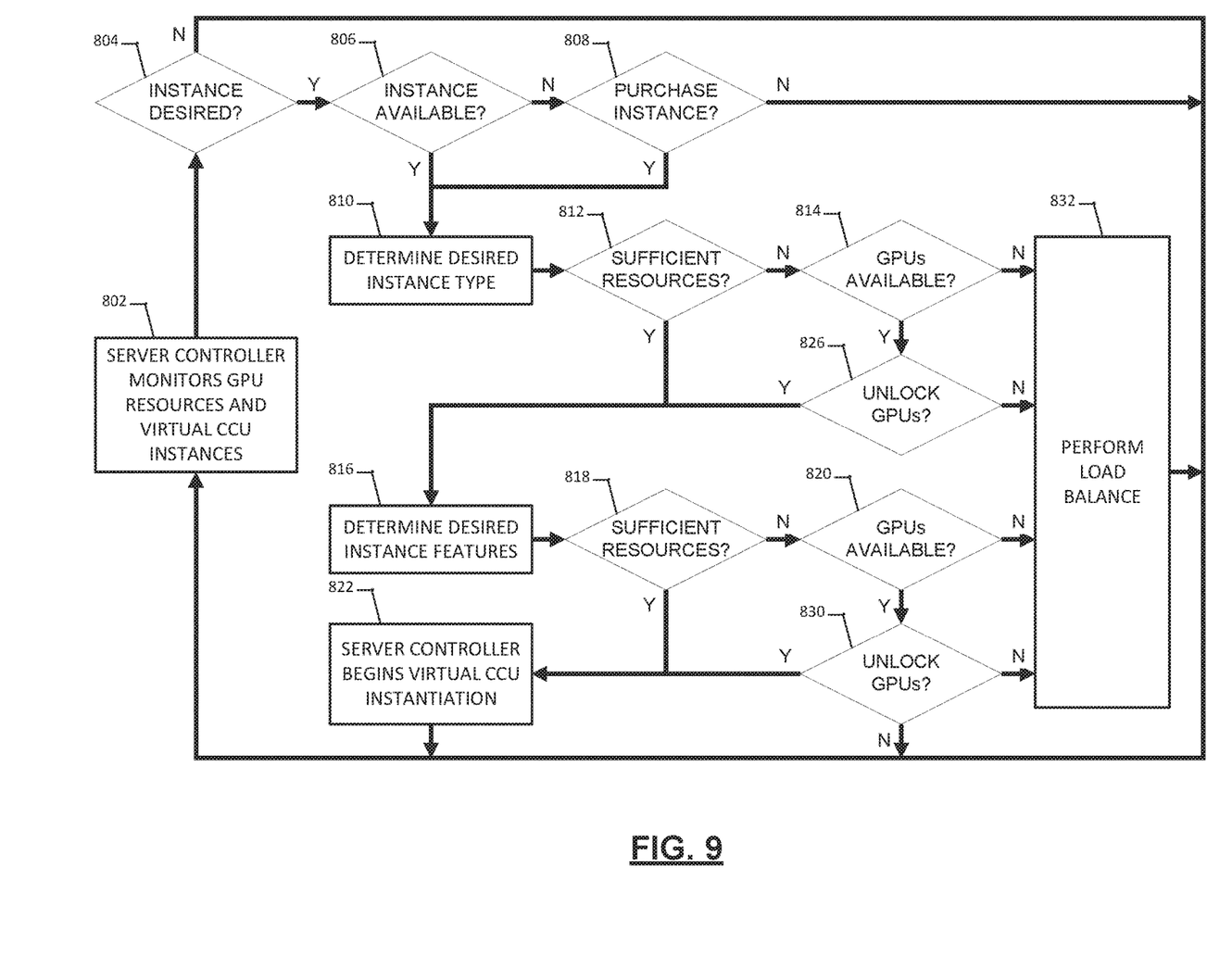
FIG. 9 is a flowchart of an exemplary embodiment of a system or controlling and allocating GPUs to a virtual CCU.
Figure 10:
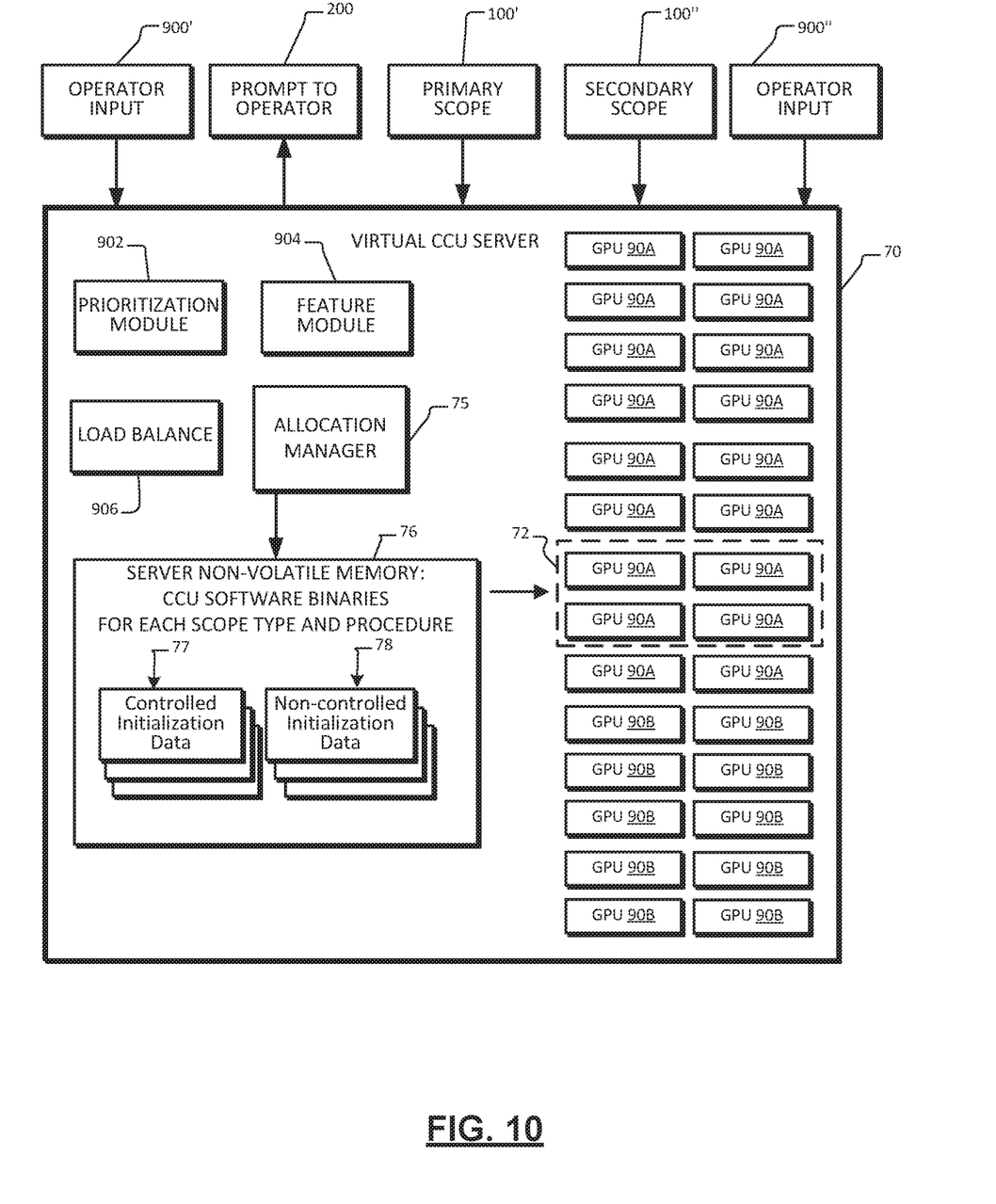
FIG. 10 is a block diagram of the virtual CCU server software architecture.

Referring now to FIGS. 8-10, flowcharts and a block diagram illustrate virtual CCU server 70 resource management of the GPUs 90 for virtual CCU 72 instantiations according to the present disclosure. As shown in FIG. 10, the virtual CCU server 70 may include various modules in addition to the allocation manager 75, including for example a prioritization module 902, a feature module 904, and a load balance module 906, Virtual CCU server 70 may include additional or fewer modules to perform the task associated with the flowcharts of FIG. 8 and FIG. 9.

With respect to FIG. 8, at step 802, the allocation manager 75 may be monitoring the resources of the virtual CCU server 70 including availability of GPUs 90 (available GPU resources) and network interfaces 110. For example, ten GPUs 90 may be present within the virtual CCU server 70 and five GPUs 90 may be in use. Likewise, five network interfaces 110 may exist within the hospital or clinic and two network interfaces 110 may be in use. The allocation manager 75 may determine an available amount of GPU resources based on how many or what portions of the GPUs 90 are available to process image data. For example, some of the GPUs may be locked, unlocked, in use, or even damaged.

At step 804, the allocation manager 75 determines whether a virtual CCU 72 instantiation is desired. For example, a primary scope 100' may be attached via a first network interface 110' in an first room 5' and send a request for a first instantiation. Alternately, an operator may log into the virtual CCU server 70 and request a first instantiation. If no instantiation is desired, the system returns to step 802 to monitor resources and await a request for a virtual CCU instantiation.

At step 806, the allocation manager 75 receives a request to start a new instantiation and determines whether an instantiation is available. For example, the hospital or clinic may be allotted a predetermined number of simultaneous virtual CCU instantiations. In one case, perhaps with three operating rooms or exam rooms, three simultaneous instantiations may be allotted. If three simultaneous instantiations are allotted and three instantiations are in use, then the allocation manager 75 may determine that there are no available instantiations and move on to step 808. However, if an instantiation is available, the allocation manager 75 may continue to step 810.

Based on attachment of the primary scope 100' or the operator provided information, the allocation manager 75 may determine an instantiation type at step 810. For example, the operator may choose a procedure or connect a specific type of primary scope 100' that indicates to the allocation manager 75 the instantiation type. The instantiation type may indicate a minimum amount of GPUs 90 necessary for the instantiation type. At step 812, the allocation manager 75 may compare the minimum amount of GPUs with the available amount of GPUs from step 802 to determine if available GPU resources are sufficient to allow the primary scope 100' to function for the instantiation type. If sufficient GPU resources are not available, the virtual CCU server 70 moves on to step 814. However, if sufficient GPU resources are available, the virtual CCU server 70 moves on to step 816.

The virtual CCU server 70 may generate a list of adjustable settings for features associated with the primary scope 100' at step 816 and determine, based on user input, what level of the settings are desired. For example, the primary scope 100' may include available features such as adjustable resolutions of video, post-processing of image data, overlaying video streams, configuring various frame rates, and the like. The user may select first levels for the settings from the list of available features, each first level within a range from a minimum level to a maximum level. For example, the primary scope 100' may include a plurality of primary scope settings of features such as resolution, frame rate, color space, color correction, imaging mode (single or multi-mode), two-dimensional to three-dimensional toggling, and other known or features at the time of this filing. The primary scope settings may initially be set to the minimum levels.

As the operator adjusts settings of the features (for example, each feature adjusted to a primary scope first level), the allocation manager 75 may determine at step 818 whether sufficient resources are available for operation of the scope 100 at the chosen levels. For example, the user may adjust primary scope settings to primary scope first levels of 4k resolution, 60 frames per second, BT2020 color space, simultaneous white light and infrared light (fluorescent imaging) imaging mode, and 3D visualization. These may be maximum levels for the primary scope settings. The operator may also adjust the levels of the settings through an iterative process. Once the primary scope settings have been set to primary scope first levels, a first desired amount of GPU resources needed to support operation of the primary scope 100' with those settings may be determined. The allocation manger 75 may compare the first desired amount of GPU resources with the available amount of GPU resources.

If after adjustment of the primary scope settings to the first levels sufficient the first desired amount of GPU resources are greater than the available amount of GPU resources, the allocation manager 75 moves on to step 820. Alternately, the virtual CCU server 70 may prompt the user to adjust decrease one or more of the primary scope settings to a lower level than the first level. However, if sufficient GPU resources are available, the allocation manager 75 moves on to step 822. At step 822, the allocation manager 75 begins a virtual CCU instantiation and returns to step 802 to monitor resources and virtual CCU instantiations.

When sufficient resources are not available at step 812, the virtual CCU server 70 may analyze the GPUs 90 to determine if any GPUs 90 are available at step 814. For example, the virtual CCU server 70 may be provided with twenty GPUs 90. However, some of the GPUs 90 may not be available for use. The allocation manager 75 may determine an amount of the GPUs 90 that are available for use by a virtual CCU 72. In some examples, a first portion of GPUs 90 may be unlocked GPUs 90A and a second portion of GPUs 90 may be locked GPUs 90B. The unlocked GPUs 90A may be allocated by the allocation manager 75 for virtual CCU instantiations and thus, may be considered an available amount of GPU resources. The locked GPUs 90B may not be allocated by the allocation manager 75 and thus, may not be considered an available amount of GPU resources.

The number of unlocked GPUs 90A versus locked GPUs 90B may depend on a service agreement with the hospital or clinic. For example, the agreement may include a number of unlocked GPUs 90A available for use based on a first subscription or payment rate. Some or all of the locked GPUs 90B may be unlocked and become available for use based on a second subscription or payment rate. Locked GPUs 90B may be unlocked during emergencies or in the event of a hardware failure such as a CPU or GPU failure. Thus, hardware may be standardized, reducing system complexities and costs. Each hospital or clinic may utilized the same system but with varying levels of GPU resources available.

The locked GPUs 90B may be unlocked remotely or by manual service through, for example, a hardware, software, or firmware upgrade. If no GPUs 90B are available to be unlocked, a hardware upgrade may be performed at step 824. If GPUs 90B are available to be unlocked, the allocation manager 75 may prompt the user to unlock additional GPUs 90B at step 826. If additional GPUs 90B are desired to be unlocked, the allocation manager 75 proceeds to step 816. Once unlocked, the previously locked GPUs 90B become unlocked GPUs 90A and are part of the available amount of GPU resources. If additional GPUs 90B are not desired to be unlocked, the server controller returns to step 802 to monitor resources and virtual CCU instantiations.

When enough GPU resources are not available at step 818, the allocation manager 75 may analyze the GPUs 90 again to determine if any additional GPUs 90 are available at step 820, similar to step 814. If GPUs 90B are not available to be unlocked, a hardware upgrade may be performed at step 828. If GPUs 90B are available to be unlocked, the allocation manager 75 may prompt the operator to unlock additional GPUs 90B at step 830. If additional GPUs 90B are unlocked, the allocation manager 75 proceeds to step 822. If additional GPUs are not desired to be unlocked, the server controller returns to step 802 to monitor resources and virtual CCU instantiations.

In other features, the virtual CCU server 70 may prioritize instantiations to balance the processing load on the GPUs 90 as shown in FIG. 9, and specifically step 832. FIG. 10 further illustrates exemplary features of virtual CCU server 70 for prioritizing at least one of virtual CCU instantiations and scope features based on available resources. For example, a first instantiation may begin at step 822 with primary scope 100' having a plurality of primary scope settings set at first levels based on operator input 900. The first instantiation may be a heart bypass surgery that may be assigned a high priority status given the gravity of the procedure, which may be determined by a prioritization module 902. The first instantiation may include primary scope 100' with a plurality of features such as two 8*k* resolution image sensors, simultaneous capture of a reflected white light image stream and a fluorescent image stream captured by the two image sensors respectively, and HDR (high dynamic range) post-processing for the white light reflected imaging.

The user may prioritize the plurality of features in order of importance. For example, resolution may be more important than HDR processing and therefore settings for resolution may be prioritized to remain at the primary scope first level while HDR settings may be adjusted. Alternately, a feature module 904 may prioritize the features based on the instantiation type or the primary scope 100'. Furthermore, as previously mentioned above, the plurality of primary scope settings may include minimum and maximum settings for acceptable operation. For example, the image sensor(s) may be capable of outputting an 8k resolution image stream but a decreased resolution selected from 480 p, 720 p, 1080 p, and 4k resolution may be acceptable for the minimum. Simultaneous display of the white light and fluorescent emitted image streams may be the maximum setting but a single image stream at a time may be acceptable for the minimum. Likewise, frame rate may be increased or decreased.

Referring back to FIG. 9, when a second instantiation may be desired at step 804 with attachment of a secondary scope 100", the allocation manager 75 may perform load balancing at step 832. Presuming a second instantiation is available at step 806, the allocation manager 75 may determine the desired instantiation type of the second instantiation. The second instantiation will generate a second desired amount of GPU resources based on a plurality of secondary scope settings being set to secondary scope first levels, similar to the primary scope 100'. For example, the second instantiation may be a bariatric surgery and include secondary scope 100" producing a 1080 p resolution video stream, white light imaging only, and no HDR processing. The second instantiation may have a lower priority than the first instantiation given the less serious nature of the procedure. In addition, the features may be prioritized in order of importance based on operator input 900, also including a minimum requirement and maximum requirement for each.

Presuming that sufficient GPU resources are unavailable for the second instantiation type at step 812, and either no additional GPUs 90 are available at step 814 or no additional GPUs 90 can be unlocked at step 826, the allocation manager 75 may be left with another option. At step 832, the allocation manager 75 may compare the primary scope settings and first type and the secondary scope settings and second instantiation to determine whether GPU resources may be rebalanced or distributed to enable both the first instantiation and the second instantiation to occur simultaneously given the total available GPU resources of the unlocked GPUs 90A. For example, if it is not desirable or possible to unlock additional GPUs 90B in steps 826 and 830 or hardware upgrades are not possible in steps 824 and 828 (from FIG. 8), the allocation manager 75 may suggest decreasing settings in use in the first instantiation to free up GPU resources for the second instantiation. Depending on the prioritization of the instantiations, the allocation manager 75 may prompt the operator of the first instantiation that a second instantiation is desired. The operator of the first instantiation may then permit or decline reallocation of GPU resources currently allocated to the first instantiation for the second instantiation to begin. The operator may choose to decrease levels of the primary scope settings to free up the GPU resources. Alternately, the feature module 904 may provide a prioritization for of the primary scope settings that may be adjusted to free up the GPU resources.

Although two simultaneous instantiations are discussed with respect to step 832, more than two instantiations with associated features could be prioritized in a variety of ways to enable automatic scope setting level reduction or suggest scope setting level reductions to one or more operators. In some examples, an operating room manager may monitor requests from various operator inputs 900 and authorize or prioritize instantiations and/or scope settings. In addition, locked GPUs 90B may be unlocked in case of emergencies, for example, during major catastrophes or hardware failure such as CPU or GPU failure.

Although a combination of such GPUs and other processors or controllers has been described, it should be apparent that other programmable logic device, digital signal processor, microcontrollers, or other digital logic circuit can be designated to perform all of the needed functions at the virtual CCU server. All of these variations can perform the same function and fall within the scope of this invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A method of operating video scopes using graphics processing unit (GPU) resources of a virtual camera control unit (CCU) server connected to a network, comprising:
   determining an available amount of GPU resources;
   providing a primary scope to connect to the network, the primary scope including a primary scope setting adjustable within a range from a minimum level that requires a minimum amount of GPU resources to a maximum level that requires a maximum amount of GPU resources;
   configuring the primary scope setting to a primary scope first level;
   determining a first desired amount of GPU resources based on the primary scope first level;
   comparing the first desired amount of GPU resources with the available amount of GPU resources;
   providing a secondary scope to connect to the network, the secondary scope including a secondary scope setting adjustable within a range from a minimum level that requires a minimum amount of GPU resources and a maximum level that requires a maximum amount of GPU resources;
   configuring the secondary scope setting to a secondary scope first level;
   determining a second desired amount of GPU resources based on the secondary scope first level;
   determining a total desired amount of GPU resources based on the first desired amount of GPU resources and the second desired amount of GPU resources; and
   comparing the total desired amount of GPU resources with the available amount of GPU resources.

2. The method of claim 1, further comprising allocating the first desired amount of GPU resources from the available amount of GPU resources when the first desired amount of GPU resources is less than or equal to the available amount of GPU resources and operating the primary scope using the primary scope first level.

3. The method of claim 1, further comprising adjusting the primary scope setting from the primary scope first level to a primary scope second level that is less than the primary scope first level when the first desired amount of GPU resources is greater than the available amount of GPU resources.

4. The method of claim 1, wherein the primary scope includes a plurality of primary scope settings, each primary scope setting adjustable within a range from a minimum level to a maximum level, further comprising prioritizing the plurality of primary scope settings in order of importance based on user input.

5. The method of claim 4, further comprising selecting a first primary scope setting of the plurality of primary scope settings based on the prioritizing and adjusting the first primary scope setting from the primary scope first level to a primary scope second level that is less than the primary scope first level.

6. The method of claim 1, further comprising prompting to increase the available amount of GPU resources when the first desired amount of GPU resources is greater than the available amount of GPU resources.

7. The method of claim 1, further comprising determining a locked amount of GPU resources, the available amount of GPU resources not including the locked amount of GPU resources.

8. The method of claim 7, further comprising prompting a user to unlock a first portion of the locked amount of GPU resources when the first desired amount of GPU resources is greater than the available amount of GPU resources.

9. The method of claim 8, further comprising determining the first portion based on a difference between the available amount of GPU resources and the first desired amount of GPU resources.

10. The method of claim 1, further comprising allocating the first desired amount of GPU resources from the available amount of GPU resources when the first desired amount of GPU resources is less than or equal to the available amount of GPU resources and operating the primary scope using the primary scope first level.

11. The method of claim 10, further comprising allocating the second desired amount of GPU resources from the available amount of GPU resources when the total desired amount of GPU resources is less than or equal to the available amount of GPU resources and operating the secondary scope using the secondary scope first level.

12. The method of claim 10, further comprising adjusting the secondary scope setting from the secondary scope first level to a secondary scope second level that is less than the secondary scope first level when the total desired amount of GPU resources is greater than the available amount of GPU resources.

13. The method of claim 10, wherein the secondary scope includes a plurality of secondary scope settings, each secondary scope setting adjustable within a range from a minimum level to a maximum level, further comprising prioritizing the plurality of secondary scope settings in order of importance based on user input.

14. The method of claim 13, further comprising selecting a first secondary scope setting of the plurality of secondary scope settings based on the prioritizing and adjusting the first secondary scope setting from the secondary scope first level to a secondary scope second level that is less than the secondary scope first level.

15. The method of claim 1, further comprising prompting to increase the available amount of GPU resources when the total desired amount of GPU resources is greater than the available amount of GPU resources.

16. The method of claim 1, further comprising determining a locked amount of GPU resources, the available amount of GPU resources not including the locked amount of GPU resources.

17. The method of claim 16, further comprising prompting a user to unlock a first portion of the locked amount of GPU resources when the total desired amount of GPU resources is great than the available amount of GPU resources.

18. The method of claim 17, further comprising determining the first portion based on a difference between the available amount of GPU resources and the total desired amount of GPU resources.

19. A system for operating video scopes using graphics processing unit (GPU) resources of a virtual camera control unit (CCU) server connected to a network, comprising:

an allocation manager that determines an available amount of GPU resources;
a primary scope including a primary scope setting, the primary scope setting adjustable within a range from a minimum level that requires a minimum amount of GPU resources to a maximum level that requires a maximum amount of GPU resources;
a secondary scope including a secondary scope setting adjustable within a range from a minimum level that requires a minimum amount of GPU resources and a maximum level that requires a maximum amount of GPU resources;
a feature module that configures the primary scope setting to a primary scope first level and the secondary scope setting to a secondary scope first level; and
a load balance module that determines a first desired amount of GPU resources based on the primary scope first level and that compares the first desired amount of GPU resources with the available amount of GPU resources, a second desired amount of GPU resources based on the secondary scope first level, and a total desired amount of GPU resources based on the first desired amount of GPU resources and the second desired amount of GPU resources, wherein the load balance module compares the total desired amount of GPU resources with the available amount of GPU resources.

20. The system of claim 19, wherein the allocation manger allocates the first desired amount of GPU resources from the available amount of GPU resources when the first desired amount of GPU resources is less than or equal to the available amount of GPU resources.

21. The system of claim 20, wherein the allocation manger allocates the second desired amount of GPU resources from the available amount of GPU resources when the total desired amount of GPU resources is less than or equal to the available amount of GPU resources.

22. The system of claim 20, wherein the feature module adjusts the secondary scope setting from the secondary scope first level to a secondary scope second level that is less than the secondary scope first level when the total desired amount of GPU resources is greater than the available amount of GPU resources.

23. The system of claim 20, further comprising a prioritization module that prioritizes a plurality of secondary scope settings in order of importance based on user input, each secondary scope setting adjustable within a range from a minimum level to a maximum level.

24. The system of claim 23, wherein the feature module selects a first secondary scope setting of the plurality of secondary scope settings based on the prioritizing and adjusts the first secondary scope setting from the secondary scope first level to a secondary scope second level that is less than the secondary scope first level.

\* \* \* \* \*